United States Patent
Wilkinson

(10) Patent No.: US 10,349,971 B2
(45) Date of Patent: Jul. 16, 2019

(54) SYSTEM AND METHOD FOR DILATING AND ADJUSTING FLEXIBILITY IN A GUIDING DEVICE

(71) Applicant: Cordis Corporation, Fremont, CA (US)

(72) Inventor: Matthew Wilkinson, Basking Ridge, NJ (US)

(73) Assignee: CARDINAL HEALTH SWITZERLAND 515 GMBh, Bar Zug (CH)

( * ) Notice: Subject to any disclaimer, the term of this patent is extended or adjusted under 35 U.S.C. 154(b) by 495 days.

(21) Appl. No.: 14/816,655

(22) Filed: Aug. 3, 2015

(65) Prior Publication Data
US 2016/0120567 A1    May 5, 2016

Related U.S. Application Data

(63) Continuation of application No. 13/232,108, filed on Sep. 14, 2011, now Pat. No. 9,095,370.
(Continued)

(51) Int. Cl.
*A61B 17/22* (2006.01)
*A61B 17/3207* (2006.01)
(Continued)

(52) U.S. Cl.
CPC ...... *A61B 17/320725* (2013.01); *A61B 17/22* (2013.01); *A61B 17/320758* (2013.01); *A61B 2017/00867* (2013.01); *A61B 2017/22038* (2013.01); *A61B 2017/22044* (2013.01); *A61B 2017/22061* (2013.01);
(Continued)

(58) Field of Classification Search
CPC .... A61B 17/320725; A61B 17/320758; A61B 2017/22038; A61B 2017/22061; A61B 2017/22094; A61M 29/00; A61M 25/0074
See application file for complete search history.

(56) References Cited

U.S. PATENT DOCUMENTS

| 4,341,210 A | 7/1982 | Elam |
| 4,898,575 A | 2/1990 | Fischell et al. |
| (Continued) | | |

FOREIGN PATENT DOCUMENTS

| CH | 668188 A5 | 12/1988 |
| CN | 2151720 Y | 1/1994 |
| (Continued) | | |

OTHER PUBLICATIONS

International Search Report for Application No. PCT/US2012/043528, dated Sep. 3, 2012, 5 pages.
(Continued)

*Primary Examiner* — Anh T Dang
(74) *Attorney, Agent, or Firm* — Nada J. Ardeleanu

(57) ABSTRACT

This disclosure is directed to systems and methods for providing a guiding device having a dilatable, drilling tip. The tip is formed by wound helical members such that resistance to rotation in an unwinding direction dilates the tip. The helical members are configured so that the dilatable tip increases in stiffness when the helical members are tensioned by a resistance to rotation in the winding direction. In some embodiments, application of relative force between coaxial inner and outer tubular members is used to control the dilation, stiffness and drilling of the guiding member.

12 Claims, 3 Drawing Sheets

Related U.S. Application Data

(60) Provisional application No. 61/502,671, filed on Jun. 29, 2011.

(51) Int. Cl.
*A61M 25/00* (2006.01)
*A61M 25/09* (2006.01)
*A61M 29/00* (2006.01)
*A61B 17/00* (2006.01)

(52) U.S. Cl.
CPC .............. *A61B 2017/22094* (2013.01); *A61M 25/0074* (2013.01); *A61M 25/0082* (2013.01); *A61M 29/00* (2013.01); *A61M 2025/09133* (2013.01); *A61M 2025/09183* (2013.01)

(56) References Cited

U.S. PATENT DOCUMENTS

| | | | |
|---|---|---|---|
| 5,071,424 A | 12/1991 | Reger | |
| 6,652,548 B2 | 11/2003 | Evans et al. | |
| 7,371,248 B2 | 5/2008 | Dapolito et al. | |
| 2005/0022809 A1 | 2/2005 | Wondka | |
| 2005/0049574 A1 | 3/2005 | Petrick et al. | |
| 2006/0184186 A1 | 8/2006 | Noone | |
| 2007/0083220 A1 | 4/2007 | Shamay | |
| 2007/0149037 A1 | 6/2007 | Souba et al. | |
| 2007/0208276 A1 | 9/2007 | Kornkven Volk et al. | |
| 2007/0208368 A1 | 9/2007 | Katoh et al. | |
| 2008/0154172 A1 | 6/2008 | Mauch | |
| 2008/0249465 A1 | 10/2008 | Ryder et al. | |
| 2008/0306499 A1 | 12/2008 | Katoh et al. | |
| 2009/0005755 A1 | 1/2009 | Keith et al. | |

FOREIGN PATENT DOCUMENTS

| | | |
|---|---|---|
| DE | 3202878 C2 | 10/1985 |
| DE | 4406077 A1 | 9/1994 |
| DE | 4032096 C2 | 3/1995 |
| DE | 29923582 U1 | 12/2000 |
| DE | 10104663 A1 | 8/2002 |
| DE | 10105592 A1 | 8/2002 |
| EP | 0257605 A1 | 3/1988 |
| EP | 0129634 B1 | 5/1988 |
| EP | 0355996 A2 | 2/1990 |
| EP | 0425361 A1 | 5/1991 |
| EP | 0427852 B1 | 7/1994 |
| EP | 0418391 B1 | 10/1995 |
| EP | 0624349 B1 | 1/1997 |
| EP | 0585757 B1 | 6/1997 |
| EP | 0623582 B1 | 1/1998 |
| EP | 0893426 A1 | 1/1999 |
| EP | 1042998 A2 | 10/2000 |
| EP | 0893426 B1 | 10/2001 |
| EP | 0744400 B1 | 9/2002 |
| EP | 1370506 A1 | 12/2003 |
| EP | 1413258 A1 | 4/2004 |
| EP | 1166710 B1 | 3/2006 |
| FR | 2859377 A1 | 3/2005 |
| FR | 2916144 A1 | 11/2008 |
| GB | 1178813 A | 1/1970 |
| GB | 2125874 A | 3/1984 |
| GB | 2305174 A | 4/1997 |
| JP | H07327916 A | 12/1995 |
| JP | H1024098 A | 1/1998 |
| JP | 2001095815 A | 4/2001 |
| WO | 9200774 A1 | 1/1992 |
| WO | 9410919 A1 | 5/1994 |
| WO | 9629027 A1 | 9/1996 |
| WO | 2004016308 A2 | 2/2004 |

OTHER PUBLICATIONS

Written Opinion of the Int'l Searching Authority for International Appln. No. PCT/US2012/043528, dated Sep. 3, 2012.
Examination Report for Australian Application No. AU2017201604 filed Mar. 8, 2017.

SYSTEM AND METHOD FOR DILATING AND ADJUSTING FLEXIBILITY IN A GUIDING DEVICE

FIELD OF THE PRESENT INVENTION

This present application is a continuation of U.S. application Ser. No. 13/232,108, filed Sep. 14, 2011, entitled "SYSTEM AND METHOD FOR DILATING AND ADJUSTING FLEXIBILITY IN A GUIDING DEVICE," now granted as U.S. Pat. No. 9,095,370, which claims priority benefit under 35 U.S.C. § 119(e) to U.S. Provisional Application No. 61/502,671, filed Jun. 29, 2011, entitled " SYSTEM AND METHOD FOR DILATING AND ADJUSTING FLEXIBILITY IN A GUIDING DEVICE," which is hereby incorporated by reference in its entirety.

The present invention relates to a guidewire or guiding catheter, and more particularly to such a device that is configured to cross a totally occluded vessel.

BACKGROUND OF THE INVENTION

Occlusive vascular disease is generally characterized by a hardened, calcified deposit blocking the flow of blood through a blood vessel. Occlusive vascular disease can cause blockages in both coronary and peripheral blood vessels. Particularly serious examples include situations in which the lesion and deposit completely block the vessel, a condition known as chronic total occlusion (CTO). A typical CTO is a lesion located in a blood vessel of a patient that results from an accumulation of deposits, typically calcified fibrin, therein.

Traditionally, this type of disease has been treated by both bypass surgery and/or drug therapy. Recently, it has been discovered that occlusive vascular disease can also be treated by advancing a guidewire through or across the diseased location to create a passageway for interventional treatment, i.e. angioplasty. Alternatively, guiding catheters intended to achieve similar functionality have also been employed. In these procedures, the guidewire is used to puncture through the hard deposit in order to create a pathway for balloon catheter or stent delivery to the lesion site. Techniques in this regard can include what is known in the art as "dottering" by which the device is subjected to short alternating advancing and retrograde movement so the tip or the like that engages the lesion site imparts short thrusts to in a sense peck away at the diseased location.

Typically, a guidewire and a catheter are separate devices that are used in percutaneous transluminal coronary angioplasty (PTCA) procedures, with the guidewire performing essentially a guiding function for the PTCA catheter that effects the desired medical procedure. Accordingly, significant challenges exist in the design of guidewires and guiding catheters. For example, positioning the guiding device at the appropriate location in the patient's anatomy is a difficult process, requiring the navigation of the tortuous vasculature and a successful crossing of the lesion while maintaining the alignment of the tip of the guiding device to prevent perforation of the vessel wall.

Further, guiding devices intended for use in CTO face additional challenges. Often, the true lumen of the vessel is embedded in the occlusion and is surrounded by false lumens that have been created over time. Attempts to cross the true lumen can result in the tip of the guiding device deflecting into the false lumens of the occlusion, which may result in vessel perforation, dissection, or release of plaque particles into the bloodstream. Moreover, during crossing, the tip of the guiding device has a natural tendency to be directed toward the side of the occlusion rather than the center due to the configuration of the occlusion, which can also result in vessel perforation, dissection and inability to cross the occlusion.

As a result, it is advantageous for guiding devices intended for use in CTO procedures with a number of functional features, some of which are opposed by nature, requiring a fine balance to be struck in order to achieve the desired performance. For example, the guiding device must be flexible enough to navigate through tortuous pathways within the body, consisting of bends, loops and branches. However, they also must be sufficiently stiff to provide the necessary pushability to overcome friction and occlusions as they are advanced into position. Guiding devices must also have sufficient stiffness to serve as a conduit for other devices that are advanced over or through them. In addition, guiding devices must be torqueable to facilitate directional changes as they are guided into position.

Therefore, a need remains for a medical device that can be easily positioned prior to and during lesion crossing and/or treatment and also reduces the risk of perforating the blood vessel. It would be advantageous to provide such a guiding device with the flexibility to be advanced through the vasculature while remaining central to the lumen of the vessel. It would also be advantageous to combine the necessary flexibility with the stiffness necessary to cross occluded lesions. Further, it would be advantageous to minimize the possibilities of the tip of guiding device deflecting off the cap of the lesion into the subintimal space. It would also be advantageous to minimize the risk of perforating the vessel wall due to misalignment of the tip of the guiding device. As will be detailed in the discussion follows, this invention satisfies these and other goals.

SUMMARY OF THE INVENTION

In accordance with the above needs and those that will be mentioned and will become apparent below, this disclosure is directed to a guiding device comprising an elongated body and a dilatable tip, wherein the tip includes a plurality of helical members having a wound configuration such that resistance to rotation in an unwinding direction dilates the tip and wherein the helical members form threads configured to provide a drilling action when the guiding device is rotated in a winding direction. Preferably, the helical members are formed from nickel-titanium alloy. The helical members are configured so that the dilatable tip increases in stiffness when the helical members are tensioned by a resistance to rotation in the winding direction.

In one embodiment, the elongated body comprises a solid guidewire. Preferably, the helical members are wound in an overlapping configuration in the noted embodiment. In another aspect, the distal tip can be configured to exhibit a deflected configuration when the helical members are untensioned and exhibit a substantially straight configuration when the helical members are tensioned.

In another embodiment, the elongated body comprises an outer tubular member disposed coaxially over an inner tubular member, wherein a proximal end of the helical members is secured adjacent a distal end of the outer tubular member and wherein a distal end of the helical members is secured adjacent a distal end of the inner tubular member. Preferably, the device also includes an elastic membrane supported by the helical members.

In one configuration, axial movement of outer tubular member with respect to inner tubular member causes the helical members to deflect radially so that the tip of the guiding device dilates. Preferably, the tip is configured so that application of axial force to outer tubular member in a proximal direction relative to inner tubular member increases stiffness in the tip. In the noted embodiments, a knob secured to a proximal end of the outer tubular member and coaxially disposed over the inner tubular member is preferably configured to allow the application of rotational and axial force to outer tubular member relative to the inner tubular member.

In another aspect, the inner tubular member further comprises a lumen configured to receive an elongated device for performing an intravascular procedure.

This invention is also directed to a method of treating occlusive vascular disease of a blood vessel, including the steps of providing a guiding device comprising an elongated body and a dilatable tip, wherein the tip includes a plurality of helical members having a wound configuration and wherein the helical members form threads, advancing the guiding device through the blood vessel until the tip is adjacent an occlusive lesion, rotating the guiding device in a winding direction so that the threads drill into the lesion, and radially displacing a portion of the lesion by rotating the guiding device in an unwinding direction to dilate the tip. Preferably, the method also includes the step of stiffening the tip by rotating the guiding device in the winding direction against resistance.

One embodiment of the method involves the use of an elongated body which features an outer tubular member disposed coaxially over an inner tubular member, wherein a proximal end of the helical members is secured adjacent a distal end of the outer tubular member, wherein a distal end of the helical members is secured adjacent a distal end of the inner tubular member. In this embodiment, the step of radially displacing the lesion preferably comprises applying a rotation force to the outer tubular member in the unwinding direction relative to the inner tubular member or applying an axial force to the outer tubular member in a distal direction relative to the inner tubular member. Further, this embodiment can include the step of stiffening the tip by applying a rotation force to the outer tubular member in the winding direction relative to the inner tubular member or by applying an axial force to the outer tubular member in a proximal direction relative to the inner tubular member.

Yet another aspect of the invention is directed to centering the guiding device in the vessel by dilating the tip. In embodiments including an inner tubular member, a further step of advancing an intravascular device through a lumen of the inner tubular member of the centered guiding device can be performed.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

At the outset, it is to be understood that this disclosure is not limited to particularly exemplified materials, architectures, routines, methods or structures as such may, of course, vary. Thus, although a number of such option, similar or equivalent to those described herein, can be used in the practice of embodiments of this disclosure, the preferred materials and methods are described herein.

It is also to be understood that the terminology used herein is for the purpose of describing particular embodiments of this disclosure only and is not intended to be limiting.

Unless defined otherwise, all technical and scientific terms used herein have the same meaning as commonly understood by one having ordinary skill in the art to which the disclosure pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise.

The total occlusion dilatable guiding device of the present invention is designed to cross a totally occluded vessel. The device comprises two means for opening and advancing through the true lumen of the vessel. A first feature is that the tip of the guiding device has a threaded, drilling or boring profile, configured to cut, dislodge, displace or break off portions of the occlusion when rotated. Preferably, this is implemented using a helical thread configuration. A second feature is that the tip of the guiding device is dilatable so that the plaque deposits forming the occlusion can be pushed away, reopening the lumen. Preferably, the distal tip has a spiral wound construction configured to expand when an unwinding torque is applied to the tip and to retract when a winding torque is applied. Another feature of this construction is that the relative flexibility of the distal tip can be changed depending upon the amount of torque exerted. These features and others can be recognized more clearly with regard to the exemplary embodiments discussed below.

Figure 1:
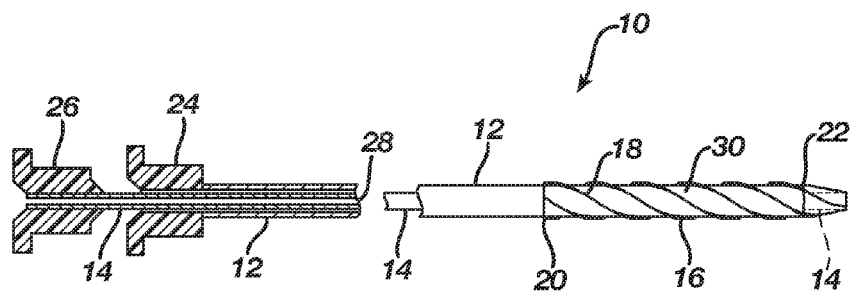
FIG. 1 is a simplified, partial cross-sectional view of an exemplary embodiment of a guiding catheter having a dilatable drilling tip, in accordance with the present invention.

Turning now to FIG. 1, a distal portion of guiding device 10 having features according to the invention is depicted schematically and partially in section. Guiding device 10 comprises an outer elongated tubular member 12 coaxially disposed over inner elongated tubular member 14. A dilatable distal tip assembly 16 includes a plurality of helical strut members 18 extending from a proximal end 20 to a distal end 22 of the tip assembly 16. The distal end of outer tubular member 12 is secured to proximal end 20 while the distal end of inner tubular member 14 extends coaxially through tip assembly 16 and is secured to distal end 22. Proximal end of outer tubular member 12 is joined to an actuating knob 24 which is coaxially disposed over inner tubular member 14. The proximal end of inner tubular member 14 terminates in a conventional hub adapter 26, allowing access to lumen 28. As will be appreciated by one of skill in the art, lumen 28 allows introduction of a wide variety of intravascular devices, including guidewires, dilation cathers, atherectomy catheters, stent-deploying catheters and the like.

As will be appreciated, actuating knob 24 allows outer tubular member 12 to be torqued relative to inner tubular member 14. Further, since actuating knob 24 is slidably disposed over inner tubular member 14, an axial force can be applied in either a distal or proximal direction at knob 24 to be transmitted to tip assembly 16. Since outer tubular member 12 is secured to proximal end 20 of tip assembly 16 and inner tubular member 14 is secured to distal end 22 of tip assembly 16, applying force in a proximal direction to knob 24 transmits an extending force to tip assembly 16 while applying force in a distal direction transmits a compressive force. Further, application of a rotational force to knob 24 transmits torque either in a winding or unwinding direction relative to helical struts 18. Correspondingly, inner tubular member 14 attachment to distal end 22 of tip assembly 16 acts to resist rotation of outer tubular member 12, creating a winding or retracting and unwinding or dilating tension in helical struts 18 depending upon the direction of rotational force applied to outer tubular member 12.

By applying differential forces to outer tubular member 12 and inner tubular member 14, tip assembly 16 can be dilated to an expanded diameter or can be retracted to increase its relative stiffness. In particular, transmitting an unwinding force or compressive force, or a combination of the two, causes the overall length of tip assembly 16 to shorten while the spiral characteristics of helical struts 18 causes their diameter to increase.

As desired, an elastic membrane 30 can be disposed over struts 18, secured to inside of struts 18, or be supported by other suitable means to help distribute the dilation forces to areas adjacent struts 18. Elastic membrane is preferably formed from biocompatible materials, including elastic polymers, such as silicones, polyamides, nylons, or a polyolefins such as polyethylene.

Figure 2:
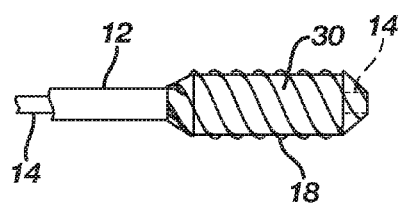
FIG. 2 is a view of the embodiment shown in FIG. 1 in a dilated configuration, according to the invention.
Figure 3:
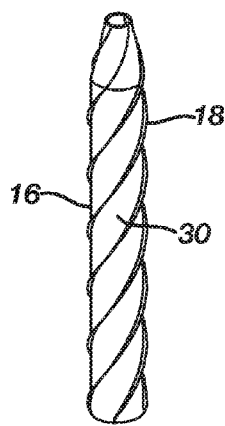
FIG. 3 is a simplified, elevational view of the dilatable tip in a retracted configuration, according to the invention.
Figure 4:
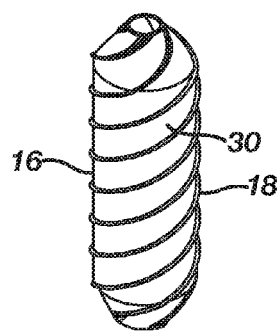
FIG. 4 is a simplified, elevational view of the dilatable tip in a dilated configuration, according to the invention.
Figure 5:
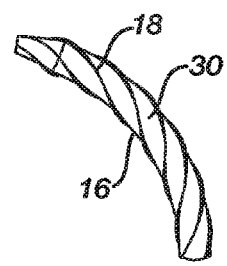
FIG. 5 is a view of the dilatable tip in the configuration shown in FIG. 3 illustrating greater flexibility that in the configuration shown in FIG. 4.

As shown in FIG. 2, tip assembly 16 dilates to an expanded configuration upon application of the pushing and/or unwinding force to knob 24. Similarly, FIGS. 3 and 4 show elevational details of tip assembly 16 in its retracted and dilated configurations, respectively. Tip assembly 16 can be returned from the dilated configuration of FIG. 4 to the retracted configuration of FIG. 3 through application of force in a proximal direction or rotational winding direction, or both, to knob 24. Additionally, as discussed below, helical members 16 can have shape memory characteristics to facilitate this process. In the retracted configuration of FIG. 3, and with no force applied to knob 24, tip assembly 16 exhibits relatively greater flexibility as shown in FIG. 5. However, further application of extension force or winding force causes a relative increase in the stiffness of tip assembly 16 as helical struts 18 are tensioned and therefore provide greater resistance to deflection. In another aspect, simultaneous rotation of outer tubular member 12 and inner tubular member 14 causes tip assembly 16 to perform a drilling or boring action. Specifically, rotation of tip assembly 16 in the winding direction causes helical struts 18 to function as drilling or cutting threads.

Figure 6:
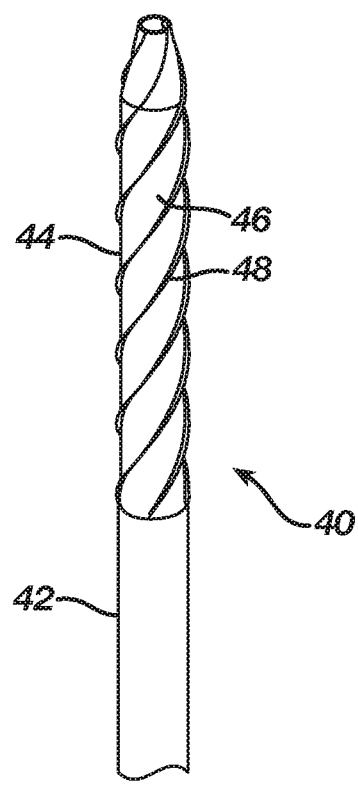
FIG. 6 is a simplified, elevational view of the distal end of a guidewire, according to the invention.
Figure 7:
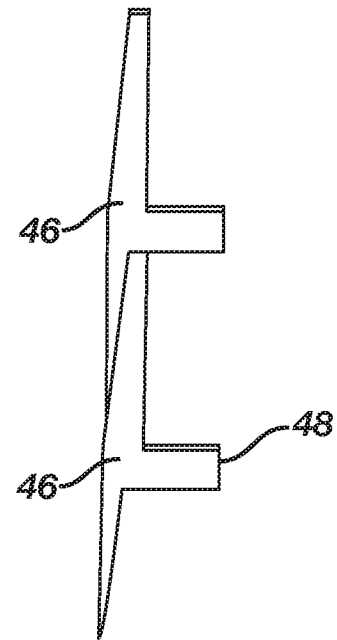
FIG. 7 is a simplified cross-sectional view of the configuration of the distal tip of the guidewire of FIG. 6, according to the invention.
Figure 8:
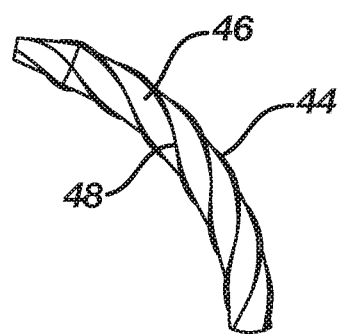
FIG. 8 is a simplified, elevational view of the distal end of a guidewire having a deflection, according to the invention.

Another dilatable guiding device embodiment of the invention is shown in FIGS. 6-8. The distal portion of dilatable guidewire 40 is shown in FIG. 6. The body of guidewire 40 comprises a conventional elongated member 42 that can have a solid core or can be a hypotube, depending upon the desired characteristics. Distal tip 44 is formed from a plurality of helical members 46, disposed in an overlapping, spiral wound configuration. FIG. 7 is a cross section view of a portion of tip 44, showing adjacent helical member 46 which are slidably engaged with each other. Cutting thread 48 operates to keep helical member 46 aligned with each other and provides a drilling or boring action when guidewire 40 is rotated in a winding direction with respect to the helical members 46.

Since helical members 46 can slide relative to each other, application of an unwinding force to distal tip 44 causes the diameter of helical members to increase, dilating tip 44. As will be appreciated, the application of an unwinding force can include advancing the distal tip 44 against a resisting obstruction, such as an occluding lesion, followed by the subsequent application of a rotating force at the proximal end of guidewire 40. When the rotating force is in an unwinding direction relative to the configuration of helical members 46, friction at the distal end of tip 44 from the lesion will cause helical members 46 to slide relative to each other, increasing their diameter and therefore, dilating tip 44. The overlapping configuration of helical members 46 maintains a relatively uniform outer surface even when dilated, facilitating travel through the lesion. When no rotational force is applied to guidewire 40, the ability of helical members 46 to slide relative to each other makes tip 44 relatively flexible, particularly as compared to a solid tip. However, when a winding force is applied, resistance experienced at the distal end of tip 44 creates tension in helical member 46, increasing the stiffness of tip 44. When sufficient rotational force is applied, the resistance caused by the lesion is overcome, resulting in the rotation of tip 44 in the winding direction and providing drilling action due to cutting threads 48.

In some embodiments, it can be desirable to configure tip 44 so that it has a directional deflected configuration such as shown in FIG. 8 when no winding tension is experienced by helical members 46. One suitable method for implementing this feature is to differentially deform or grind one or more of helical members 46. As will be appreciated, such a configuration provides guidewire 40 with improved steerability for navigation through a patient's vasculature. When tension is applied to helical members 46 through resistance to rotation, tip 44 assumes a substantially straight configuration to facilitate drilling and advancing through the occluding lesion.

In presently preferred embodiments of the invention, helical members 18 and 46 are formed from a nickel-titanium alloy such as Nitinol. As known to those of skill in the art, these alloys can exhibit shape memory and/or superelastic characteristics. Generally, shape memory allows the member to be deformed to secondary configuration, but when heated will return to its original configuration. Superelastic characteristics, on the other hand, generally allow the metal to be placed under strain and deformed, causing a phase transformation. Once the strain is removed, the superelastic member will change phase and return to its original shape. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal to a temperature above which the transformation from the martensite phase to the austenite phase is complete, i.e. a temperature above which the austenite phase is stable (the Af temperature). The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape if unrestrained. If restrained, the metal will remain martensitic until the restraint is removed.

When stress is applied to a specimen of a metal, such as Nitinol, exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. These properties are particularly suitable to the winding and unwinding action of helical members 18 and 46 to effect the dilation and retraction of tip 16 and 42.

Figure 9:
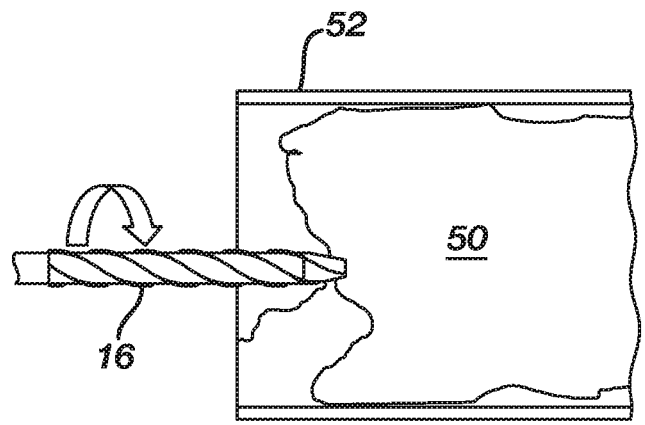
FIG. 9 is a schematic view of a guiding device of the invention drilling an occluding lesion, according to the invention.
Figure 10:
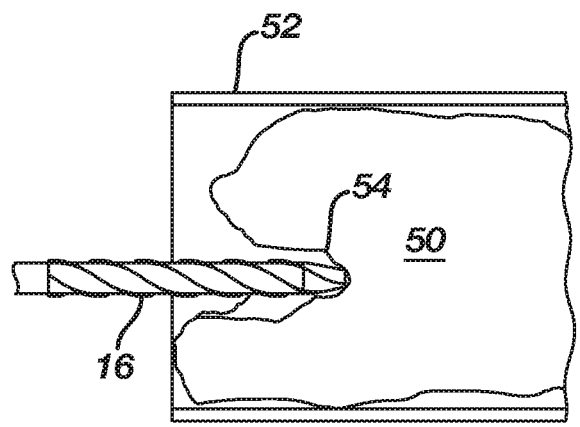
FIG. 10 is a schematic view of a guiding device of the invention being advance into an occluding lesion, according to the invention.
Figure 11:
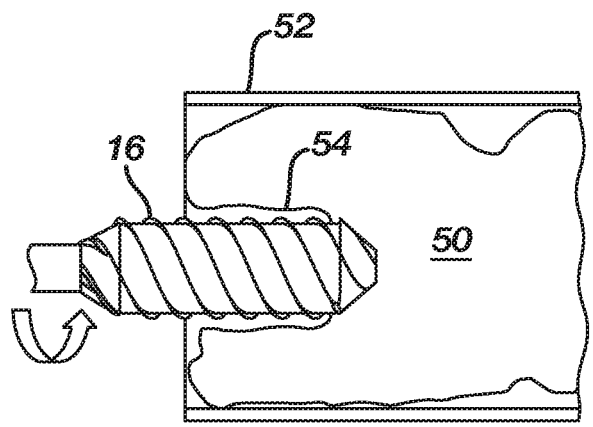
FIG. 11 is a schematic view of a guiding device of the invention, radially displacing a portion of the lesion by dilating the tip, according to the invention.

Operation of the guiding devices of the invention is shown schematically in FIGS. 9-11, which feature guiding catheter 10. One of skill in the art will recognize that guidewire 40, as well as other embodiments of the invention, can provide similar functionality. FIG. 9 shows the tip assembly 16 of guiding catheter 10 having been advanced through a patient's vasculature to an occluding lesion 50 within the lumen of vessel 52. At this point, tip assembly 16 is in contact with lesion 50. Simultaneous rotation of inner tubular member 14 and outer tubular member 12 causes tip assembly 16 to drill into lesion 50. As discussed above, application of rotational or axial forces to outer tubular member 12 relative to inner tubular member 14 changes the stiffness profile of tip assembly 16, aiding the advancement of guiding catheter 10 into a microchannel or by penetrating the calcified cap of lesion 50. As shown in FIG. 10, continued drilling rotation of guiding catheter 10 allows the formation of a channel 54 through lesion 50.

As desired, tip assembly 16 can be dilated as shown in FIG. 11. This can be effected by applying the appropriate rotational or axial force to outer tubular member 12 relative to inner tubular member 14 as described above. Expansion of the tip assembly 16 applies a radial force to lesion 50, pushing the plaque away to increase the diameter of channel 54 and to facilitate the further advancement of guiding catheter 10. Moreover, applying an overall unwinding rotational force to catheter 10 will also tend to cause tip assembly 16 to dilate. Dilation of tip assembly 16 tends to center guiding catheter 10 within vessel 52. This facilitates the process of creating channel 54 within the true lumen and can also stabilize guiding catheter 10, such that an intravascular device advanced through lumen 28 will be positioned in the correct orientation towards the center of the lesion and will further minimize the risk of the intravascular device being deflected by cap of the lesion.

In operation, the use of guidewire 40 generally follows the same procedures. Specifically, when rotated in a winding direction, resistance from the lesion will cause an increase in tension of helical member 46, stiffening tip 44. Thus, by varying the amount of torque applied to guidewire 40, the operator can adjust the relative flexibility of tip 44 once it is in contact with the lesion. Rotation of guidewire 40 in the winding direction that overcomes the lesion's resistance will cause a drilling action that can be employed to create or enlarge a channel through which to advance guidewire 40 through the lesion. Correspondingly, rotation of guidewire 40 in the unwinding direction will create an expansion of tip 44, due to the friction of the lesion resisting the rotation of the distal end of tip 44, and this dilation causes a radial displacement of plaque in the lesion.

As will be appreciated, chief differences between guiding catheter 10 and guidewire 40 are that the guiding catheter offers relatively greater control over dilation and tip stiffness through the application of differential forces to outer tubular member 12 and inner tubular member 14 while guidewire 40 offers a lower profile and simplified manufacture.

In general, the combination of dilation and drilling actions allow the guiding devices of the invention to cross CTO lesions while also creating a large enough channel to allow introduction of other intravascular devices, such as stent delivery catheters or dilation catheters. Since the helical members allow the stiffness of the tip to be increased, the native flexibility in the absence of rotational or axial tension can be greater to facilitate intraluminal steering. Correspondingly, once greater pushability is desired, tip stiffness can be increased through application of rotational or axial tension to facilitate crossing calcified lesions. The drilling actions of the guiding devices allow for more direct penetration of the cap of the occlusion, minimizing the tendency of the hardened cap to deflect intravascular devices being advanced into subinitimal locations. Further, dilation of the tip also helps center the device within the lumen of the patient's vessel, which also minimizes subintimal trapping and vessel perforation.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A guiding device comprising an elongated body and a dilatable tip, wherein the tip includes a plurality of helical members having a wound construction configured to radially expand when an unwinding torque is applied to the tip and to radially retract when a winding torque is applied to the tip, such that resistance to rotation in an unwinding direction dilates the tip, and wherein the helical members form threads configured to provide a drilling action when the guiding device is rotated in a winding direction; and
wherein the elongated body comprises an outer tubular member disposed coaxially over an inner tubular member and a knob secured to a proximal end of the outer tubular member.

2. The guiding device of claim 1, wherein the helical members are formed from a nickel-titanium alloy.

3. The guiding device of claim 1, wherein the dilatable tip is configured to increase in stiffness when the helical members are tensioned by a resistance to rotation in the winding direction.

4. The guiding device of claim 1, wherein the elongated body comprises a solid guidewire.

5. The guiding device of claim 4, wherein the helical members are wound in an overlapping configuration.

6. The guiding device of claim 4, wherein the distal tip is configured to exhibit a deflected configuration when the helical members are untensioned and exhibit a substantially straight configuration when the helical members are tensioned.

7. The guiding device of claim 1, wherein a proximal end of the helical members is secured adjacent a distal end of the outer tubular member and wherein a distal end of the helical members is secured adjacent a distal end of the inner tubular member.

8. The guiding device of claim 7, further comprising an elastic membrane supported by the helical members.

9. The guiding device of claim 7, wherein axial movement of the outer tubular member with respect to the inner tubular member causes the helical members to deflect radially so that the tip of the guiding device dilates.

10. The guiding device of claim 7, wherein the tip is configured so that application of axial force to the outer tubular member in a proximal direction relative to the inner tubular member increases stiffness in the tip.

11. The guiding device of claim 7 wherein the knob is coaxially disposed over the inner tubular member and is configured to allow the application of rotational and axial force to the outer tubular member relative to the inner tubular member.

12. The guiding device of claim 7, wherein the inner tubular member further comprises a lumen configured to receive an elongated device for performing an intravascular procedure.

* * * * *